(12) United States Patent
Liu et al.

(10) Patent No.: US 9,403,747 B2
(45) Date of Patent: Aug. 2, 2016

(54) METHODS AND COMPOSITIONS FOR TREATING LEUKEMIA

(71) Applicant: Golden Biotechnology Corporation, Jersey City, NJ (US)

(72) Inventors: Sheng-Yung Liu, New Taipei (TW); Wu-Che Wen, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 86 days.

(21) Appl. No.: 14/184,982

(22) Filed: Feb. 20, 2014

(65) Prior Publication Data

US 2015/0025135 A1    Jan. 22, 2015

Related U.S. Application Data

(60) Provisional application No. 61/767,211, filed on Feb. 20, 2013.

(51) Int. Cl.
| | |
|---|---|
| *A61K 31/12* | (2006.01) |
| *C07C 49/753* | (2006.01) |
| *A61K 31/122* | (2006.01) |
| *A61K 31/133* | (2006.01) |
| *A61K 31/365* | (2006.01) |
| *A61K 31/7034* | (2006.01) |
| *C07C 50/28* | (2006.01) |
| *C07C 59/90* | (2006.01) |
| *C07D 307/33* | (2006.01) |
| *A61K 9/00* | (2006.01) |
| *A61K 9/48* | (2006.01) |
| *A61K 36/07* | (2006.01) |

(52) U.S. Cl.
CPC ............. *C07C 49/753* (2013.01); *A61K 9/0056* (2013.01); *A61K 9/0078* (2013.01); *A61K 9/4858* (2013.01); *A61K 31/122* (2013.01); *A61K 31/133* (2013.01); *A61K 31/365* (2013.01); *A61K 31/7034* (2013.01); *C07C 50/28* (2013.01); *C07C 59/90* (2013.01); *C07D 307/33* (2013.01); *A61K 36/07* (2013.01); *C07C 2101/16* (2013.01)

(58) Field of Classification Search
CPC ...................................................... A61K 31/12
USPC .......................................................... 514/690
See application file for complete search history.

(56) References Cited

U.S. PATENT DOCUMENTS

| | | | | |
|---|---|---|---|---|
| 5,905,089 A | * | 5/1999 | Hwang | ................ A61K 31/365 514/468 |
| 2007/0287672 A1 | * | 12/2007 | Creighton | .............. A61K 31/10 424/70.11 |
| 2013/0005825 A1 | | 1/2013 | Liu et al. | |
| 2015/0018296 A1 | * | 1/2015 | Liu | .................... A61K 31/7064 514/43 |

OTHER PUBLICATIONS

Choi, et al., "Apoptosis induction of U937 human leukemia cells by dially trisulfide induces through generation of reactive oxygen species", J. of Biomedical Science 2012, 19:50 1-11.

* cited by examiner

*Primary Examiner* — Raymond Henley, III
(74) *Attorney, Agent, or Firm* — Chang-Hsing Liang

(57) ABSTRACT

The present invention provides methods and compositions for treating leukemia by cyclohexenone compounds.

20 Claims, 10 Drawing Sheets

METHODS AND COMPOSITIONS FOR TREATING LEUKEMIA

BACKGROUND OF THE INVENTION

Leukemia (leukaemia) is a type of cancer of the blood or bone marrow characterized by an abnormal increase of immature white blood cells called "blasts". Leukemia is a broad term covering a spectrum of diseases. In turn, it is part of the even broader group of diseases affecting the blood, bone marrow, and lymphoid system, which are all known as hematological neoplasms.

Clinically and pathologically, leukemia is subdivided into a variety of large groups. The first division is between its acute and chronic forms. Acute leukemia is a family of serious medical conditions relating to an original diagnosis of leukemia. Forms of acute leukemia include: acute myeloid leukemia, acute erythroid leukemia, acute lymphoblastic leukemia, T-cell acute lymphoblastic leukemia, adult T-cell leukemia/lymphoma, precursor T acute lymphoblastic leukemia/lymphoma, blast crisis of chronic myelogenous leukemia. Chronic leukemia is an increase of abnormal white blood cells. It differs from acute leukemia, and is categorized as myelogenous or lymphocytic. Chronic leukemia may refer to: chronic myelogenous leukemia, chronic lymphocytic leukemia, hairy cell leukemia. Additionally, the diseases are subdivided according to which kind of blood cell is affected. This split divides leukemias into lymphoblastic or lymphocytic leukemias and myeloid or myelogenous leukemias.

SUMMARY OF THE INVENTION

In one aspect provided herein are methods for treating or reducing the risk of leukemia in a subject comprising administering to said subject a therapeutically effective amount of a cyclohexenone compound having the structure:

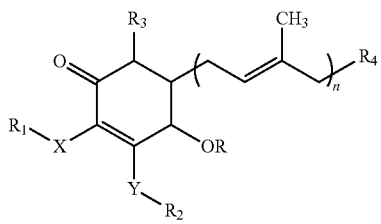

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, optionally substituted methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 2:
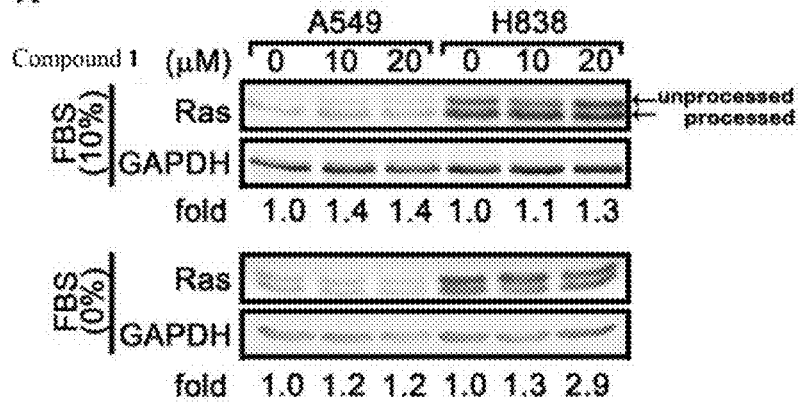
FIG. 2A-C show illustrative effective results of the exemplary Compound 1 inhibiting Ras processing in cancer cell lines. (2A) A549 and H838 cells were treated with different concentrations of Compound 1 and grown under serum (10% FBS) or serum-free (no FBS) conditions for 24 h. (2B) H838, (2C) HepG2 and K562 cells were treated with different concentrations of Compound 1 and grown under serum-free (no FBS) conditions for 24 h. Whole cell lysates were then immunoblotted with a Ras antibody. A duplicate membrane was probed with a GAPDH antibody. The relative expression level of unprocessed to processed Ras was quantified by densitometry. The experiments were conducted three times. Bars represent the mean±SEM. *P<0.05, ** P<0.01
Figure 2:
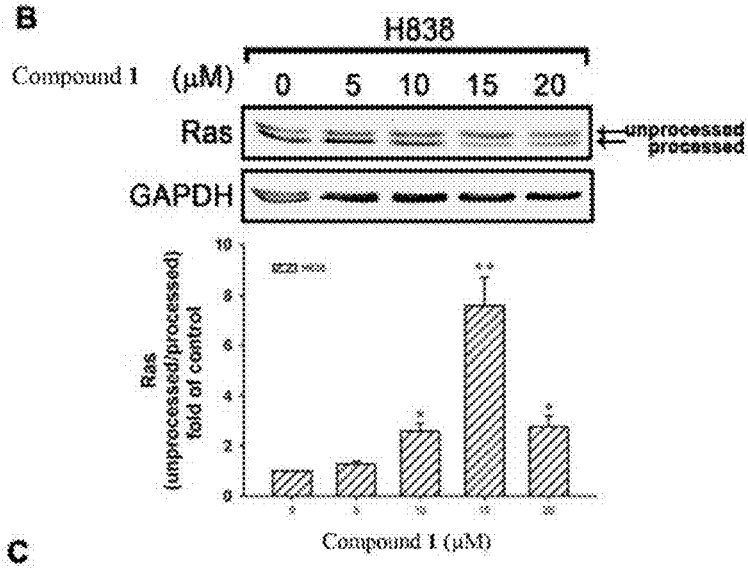
Figure 2:
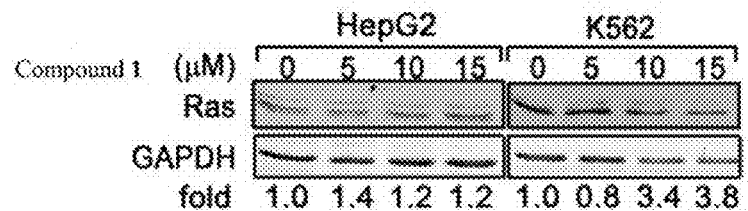

Ras proteins are small GTPases that appear to be engaged in multiple signaling pathways, leading to complex and divergent effects. Activation of Ras proteins is regulated by post-translational modification, which includes FTase-mediated prenylation of Ras. Prenylation is essential for the normal function and transforming activity of the Ras superfamily of proteins. Thus, agents that block Ras prenylation have been developed to interfere with cancer cell survival and proliferation. Exemplary Compound 1 described herein is a novel farnesylated quinone derivative isolated from *Antrodia camphorate*. Docking studies showed that the farnesyl isoprenoid tail of Compound 1 inserts into the central cavity of the FTase β-subunit similar to the farnesyl group of FPP (See FIG. 5). FTase inhibition assays revealed that Compound 1 inhibited FTase in a dose-dependent manner in vitro (See Example 10) Furthermore, the ratio of unprocessed to processed Ras increased after Compound 1 administration (See FIG. 2). All of these data support that exemplary Compound 1, and the like interact with FTase to prevent Ras processing inside cancer cells.

The $IC_{50}$ values of Compound 1 in cancer cell lines described herein have been shown to correlate with expression of Ras and the epidermal growth factor receptor (EGFR). The data described herein suggests that the protein level of Ras and EGFR, rather than the presence of mutations in the Ras and EGFR genes, is the major determinant of Antroquinonol-induced cytotoxicity in cancer cells.

Figure 7:
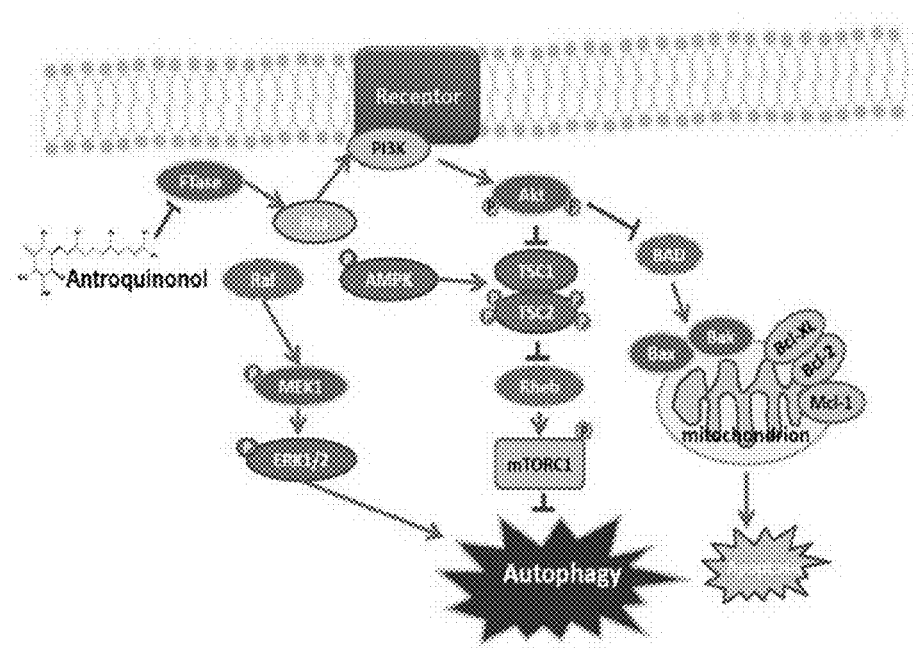
FIG. 7 shows an exemplary schematic diagram illustrating the proposed mechanism of action of Compound 1. Lines with end arrows indicate activation and up-regulation, whereas those with perpendicular bars at the end indicate inhibition and down-regulation. A gray color with a dotted circle indicates molecules that have not been validated. Dashed edges indicate interactions that have not been validated. "P" indicates phosphorylation.

The molecular modeling and docking-based approaches were used to demonstrate the possibility of interaction between GGTase-I and Compound 1. The previous studies revealed that Compound 1 triggers antitumor activity through several signaling molecules including AMPK, PI3K, and mTOR (see e.g., Kumar V B, et al., Mutat Res 2011 Feb. 10; 707(1-2):42-5229; Yu C-C, et al., The Journal of nutritional biochemistry 23 (8):900-907; Chiang P-C, et al., Biochemical Pharmacology 79 (2):162-171). Here, in some embodiments provide the exemplary cyclohexenone compounds (e.g., Compound 1) inhibiting Ras processing through inhibition of FTase activity. The possible signaling pathways that contribute to Compound 1-mediated antitumor activity are summarized in FIG. 7. The Ras-PI3K-Akt-mTOR pathway, which is associated with proliferation, motility, metabolism, and differentiation, is inhibited in response to Compound 1. Other key signaling molecules, such as ERK1/2 and AMPK, were induced in response to Compound 1 treatment. Several studies have found that ERK1/2 and AMPK are involved in different aspects of apoptotic and autophagic cell death. It is inferred that multiple signaling pathways are simultaneously activated in response to Compound 1 stimulation. Thus, in some embodiments, the cyclohexenone compounds provided herein (e.g., Compound 1) promote the anticancer effects by regulating cross talk in a complex signaling network that results in apoptosis and autophagy.

Inhibition of prenyltransferase activity suppresses prenylation of multiple signaling molecules, interfering with downstream signaling. Ras is a pivotal signaling protein in a complex network that regulates several aspects of normal cell growth and malignant transformation. Activating mutations in Ras, especially K-Ras, frequently occur in human cancers. Thus, targeting Ras is a promising strategy for treating cancer. Based on the biochemical characterization and molecular docking analysis, the cyclohexenone compounds provided herein (e.g., Compound 1) inhibit Ras processing via inhibition of the enzyme farnesyltransferase, ultimately resulting in cell death.

Leukemia is a malignant cancer of the bone marrow and blood. It is characterized by the uncontrolled growth of blood cells. Acute leukemia is a rapidly progressing disease that results in the massive accumulation of immature, functionless cells in the marrow and blood. The marrow often can no longer produce enough normal red and white blood cells and platelets. Anemia, a deficiency of red cells, develops in virtually all leukemia patients. The lack of normal white cells impairs the body's ability to fight infections. A shortage of platelets results in bruising and easy bleeding. On the other hand, chronic leukemia progresses more slowly and leads to unregulated proliferation and hence marked overexpansion of a spectrum of mature (differentiated) cells.

In some embodiments, provided herein are methods for treating or reducing the risk of a subject with leukemia by administering a cyclohexenone compound described herein to the subject (e.g. a human). The cyclohexenone compounds provide therapeutic benefit to a subject being treated for leukemia (see Examples 1-13). The cyclohexenone compounds, in some embodiments, are obtained from extracts of natural products and provide reduced complications and/or side effects. In some embodiments, this invention provides the therapeutic and prophylactic potential of exemplary cyclohexenone compounds (e.g., Compound 1) for treating or reducing the risk of leukemia.

In some embodiments, there are provided methods for treating or reducing the risk of a subject with leukemia comprising administering to said subject a therapeutically effective amount of a cyclohexenone compound having the structure:

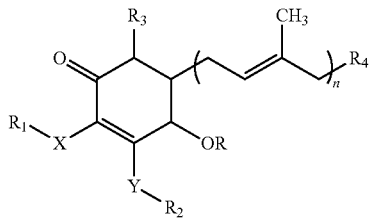

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the leukemia is an acute leukemia such as an acute myeloid leukemia, acute erythroid leukemia, acute lymphoblastic leukemia, T-cell acute lymphoblastic leukemia, adult T-cell leukemia/lymphoma, precursor T acute lymphoblastic leukemia/lymphoma, or blast crisis of chronic myelogenous leukemia. In some embodiments, the leukemia is chronic leukemia such as a chronic myelogenous leukemia, chronic lymphocytic leukemia, hairy cell leukemia. In certain embodiments, the chronic leukemia is a chronic myelogenous leukemia. In some embodiments, the subject is human. See Examples 2-13.

In some embodiments, the cyclohexenone compound having the structure

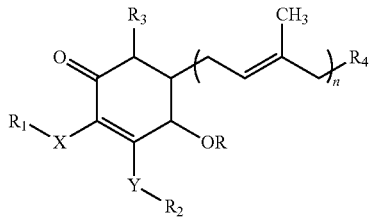

is prepared synthetically or semi-synthetically from any suitable starting material. In other embodiments, the cyclohexenone compound is prepared by fermentation, or the like. For example, Compounds 1, and 3-7 are isolated from organic solvent extracts. The non-limited exemplary compounds are illustrated below.

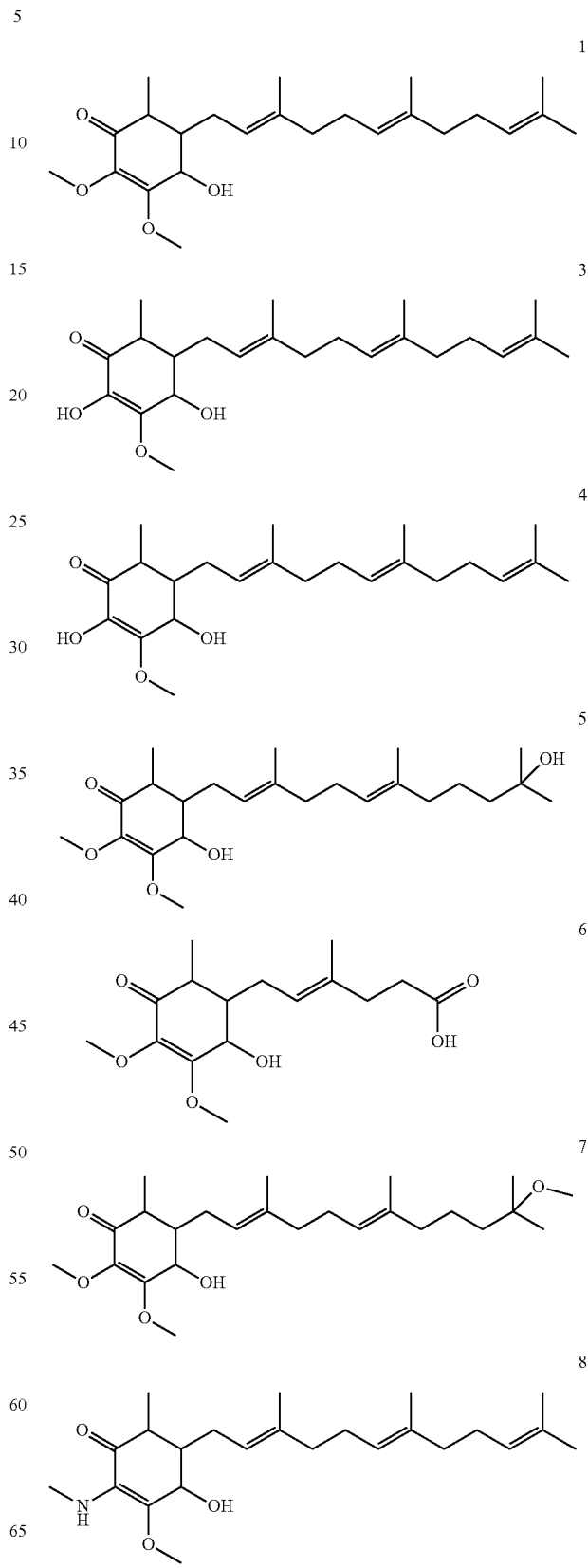

2
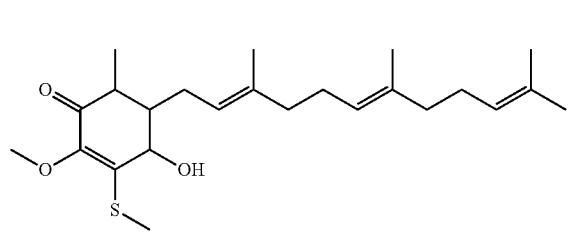
9
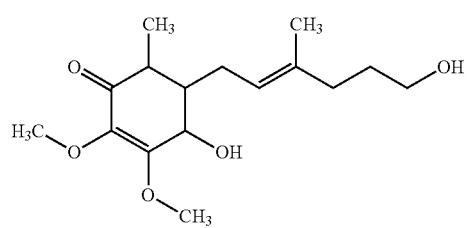
10
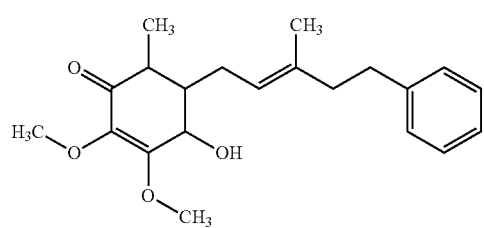
11
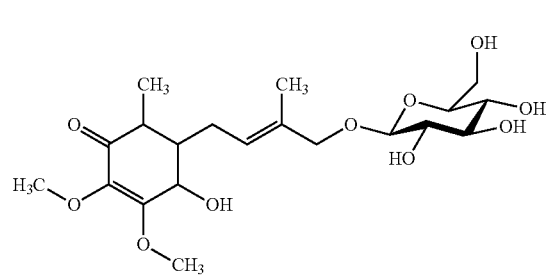
12
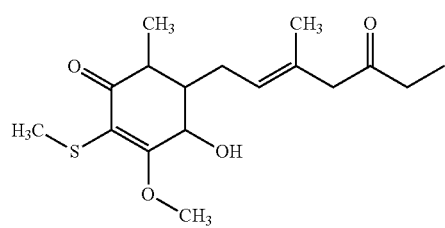
13
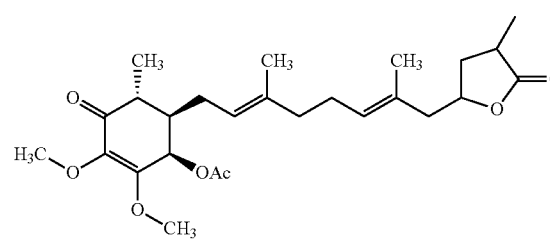
14
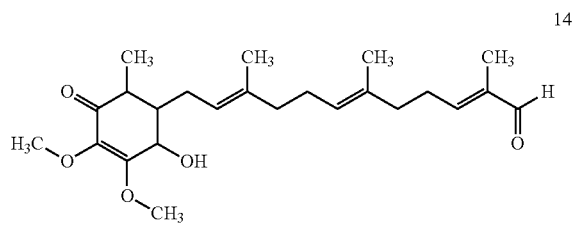
15
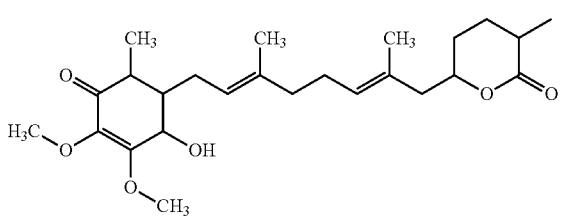
16
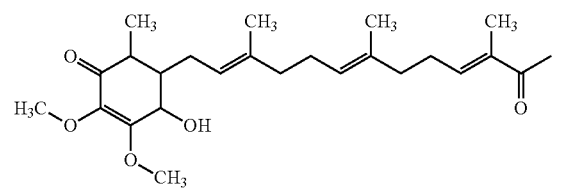
17
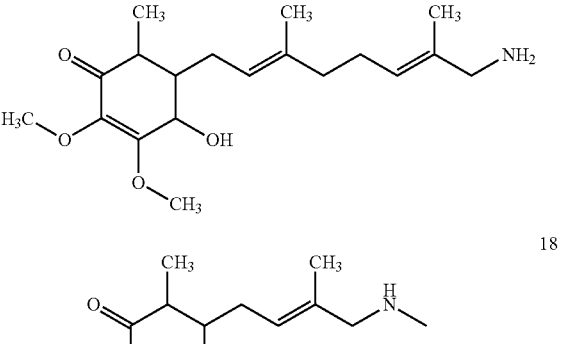
18
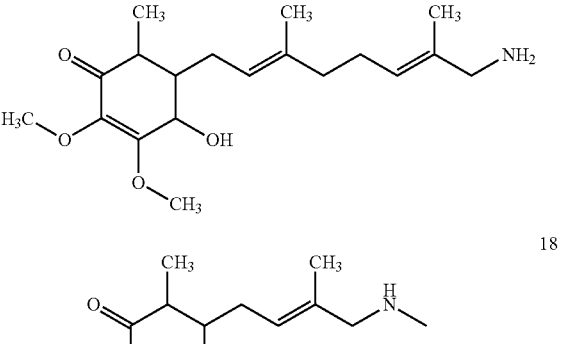
19
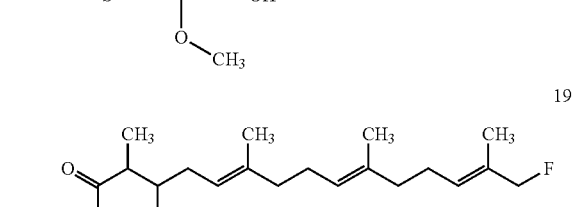
20
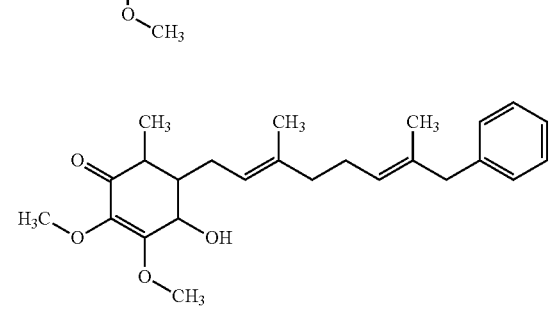

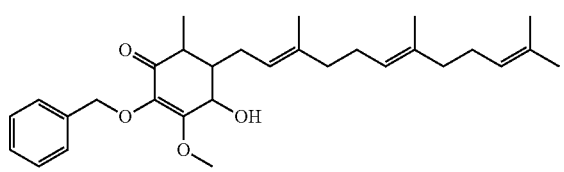

21

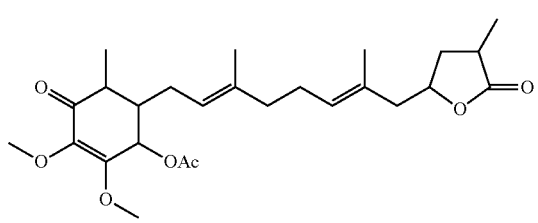

22

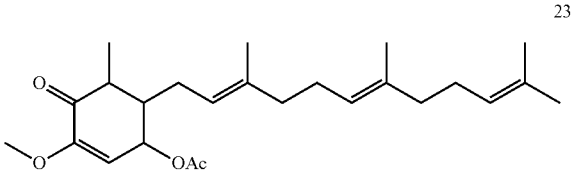

23

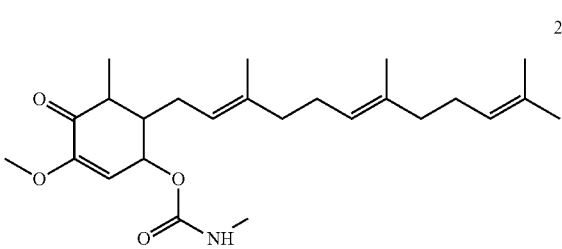

24

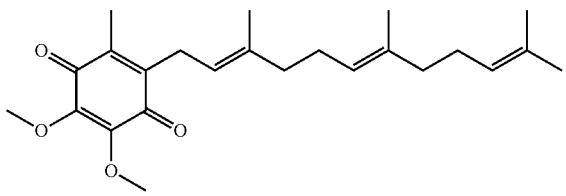

25

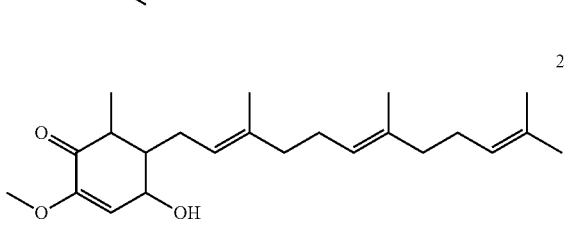

26

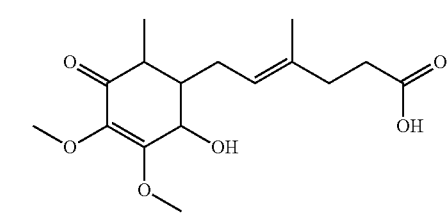

27

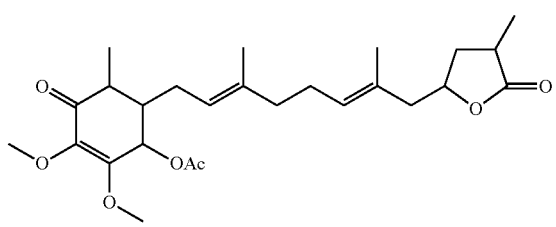

28

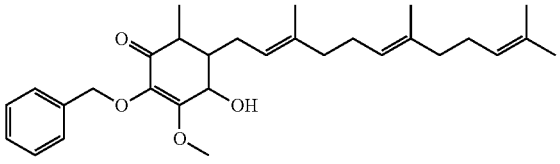

29

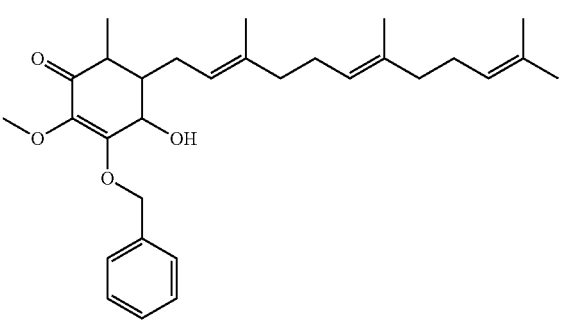

30

31

In other embodiments, the cyclohexenone compound having the structure

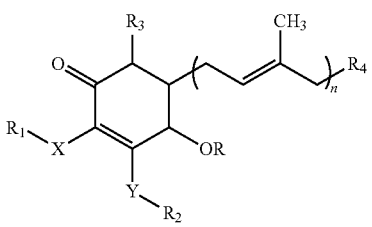

is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, C(=O)C$_3$H$_8$, C(=O)C$_2$H$_5$, or C(=O)CH$_3$. In some embodiments, R$_1$ is a hydrogen or methyl. In certain embodiments, R$_2$ is a hydrogen, methyl, ethyl, propyl, butyl, pentyl or hexyl. In some embodiments, R$_3$ is a hydrogen, methyl, ethyl, propyl, butyl, pentyl or hexyl. In some embodiments, R$_4$ is halogen, NH$_2$, NHCH$_3$, N(CH$_3$)$_2$, OCH$_3$, OC$_2$H$_5$, C(=O)CH$_3$, C(=O)C$_2$H$_5$, C(=O)OCH$_3$, C(=O)OC$_2$H$_5$, C(=O)NHCH$_3$, C(=O)NHC$_2$H$_5$, C(=O)NH$_2$, OC(=O)CH$_3$, OC(=O)C$_2$H$_5$, OC(=O)OCH$_3$, OC(=O)OC$_2$H$_5$, OC(=O)NHCH$_3$, OC(=O)NHC$_2$H$_5$, or OC(=O)NH$_2$. In some embodiments, R$_4$ is C$_2$H$_5$C(CH$_3$)$_2$OH, C$_2$H$_5$C(CH$_3$)$_2$OCH$_3$, CH$_2$COOH, C$_2$H$_5$COOH, CH$_2$OH, C$_2$H$_5$OH, CH$_2$Ph, C$_2$H$_5$Ph, CH$_2$CH=C(CH$_3$)(CHO), CH$_2$CH=C(CH$_3$)(C(=O)CH$_3$), 5 or 6-membered lactone, C$_2$-C$_8$alkenyl, C$_2$-C$_8$alkynyl, aryl, and glucosyl, wherein 5 or 6-membered lactone, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl. In certain embodiments, R$_4$ is CH$_2$CH=C(CH$_3$)$_2$. In certain embodiments, the compound is

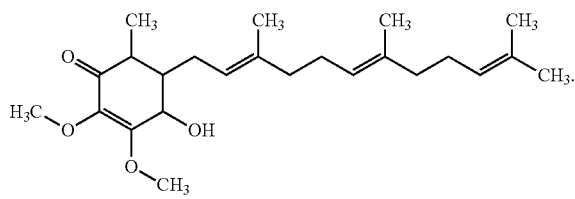

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "C$_1$-C$_8$ alkyl" or similar designations. By way of example only, "C$_1$-C$_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a C$_1$-C$_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a C$_1$-C$_{12}$alkylene. In another aspect, an alkylene is a C$_1$-C$_8$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a C$_6$-C$_{10}$aryl. Depending on the structure, an aryl group can be a monoradical or a diradical (i.e., an arylene group). In one aspect, an arylene is a C$_6$-C$_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkynyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

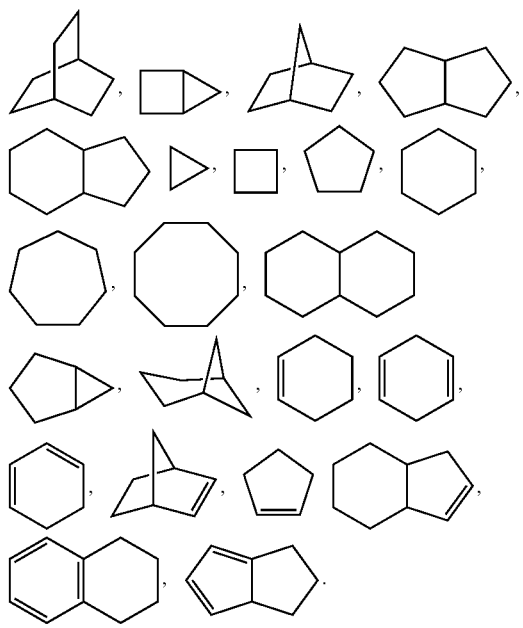

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration and Dosage

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Pharmaceutical Formulation

In some embodiments provide pharmaceutical compositions comprising a therapeutically effective amount of a cyclohexenone compound having the structure:

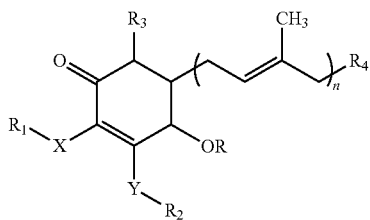

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and a pharmaceutically acceptable excipient.

In some embodiments, the cyclohexenone compounds of the pharmaceutical compositions have the structure:

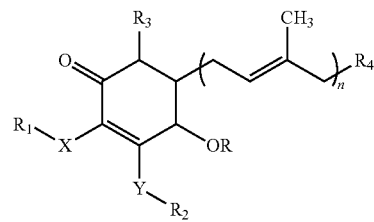

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein the 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

In certain embodiments, the compound is selected from group consisting of

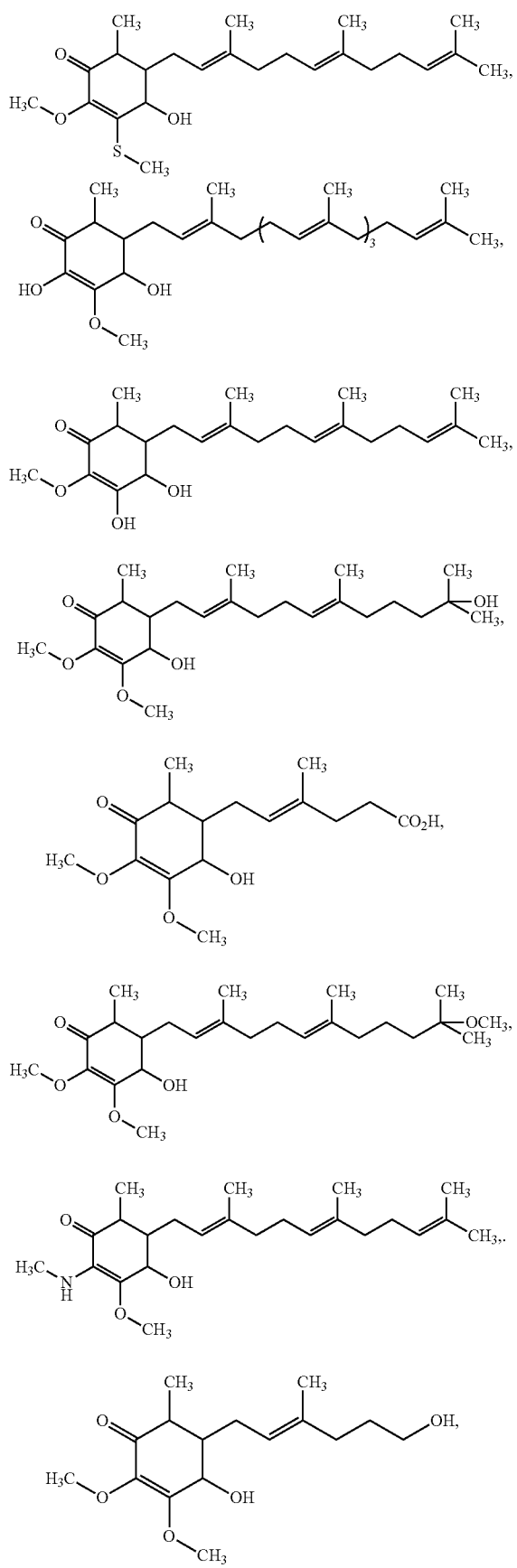
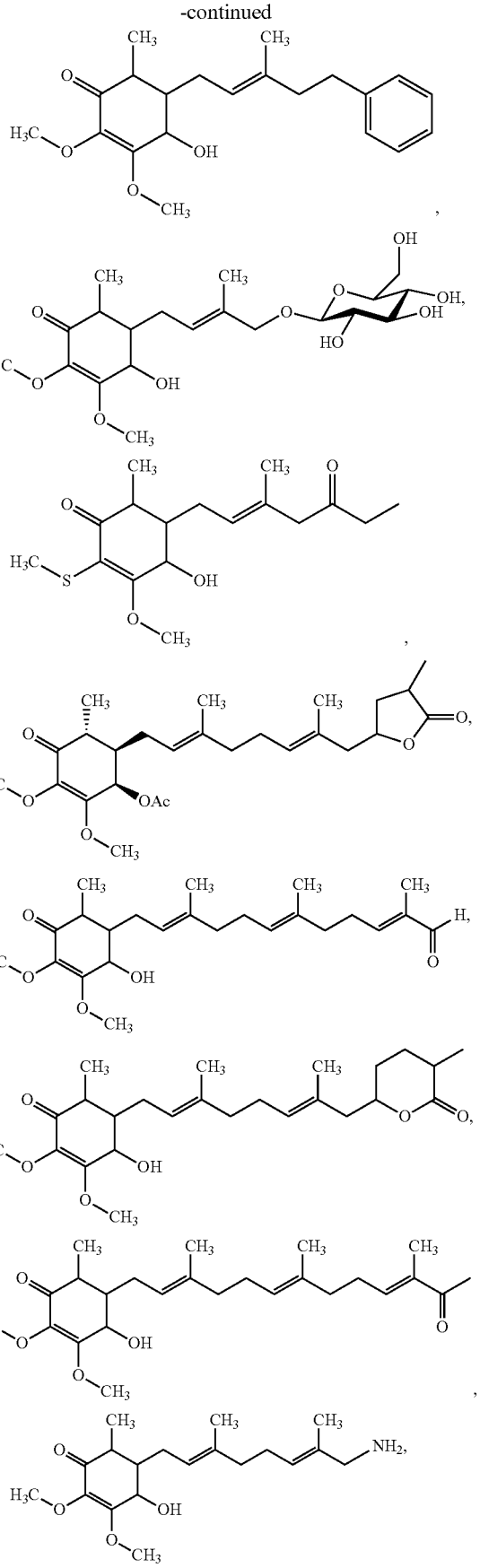

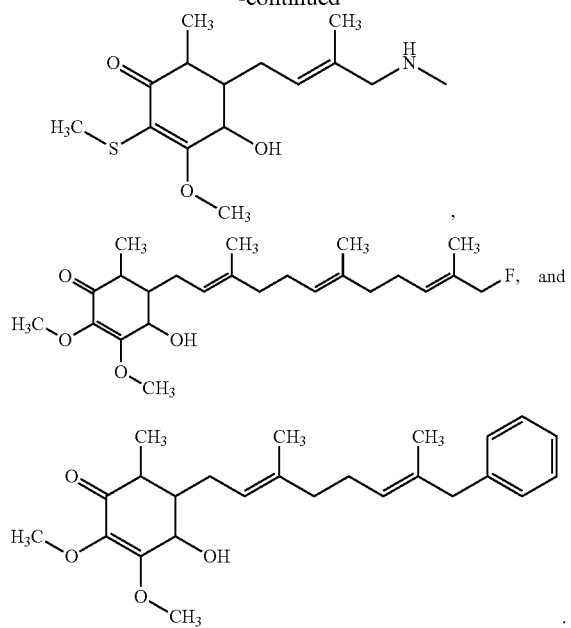
In certain embodiments, the compound is selected from group consisting of
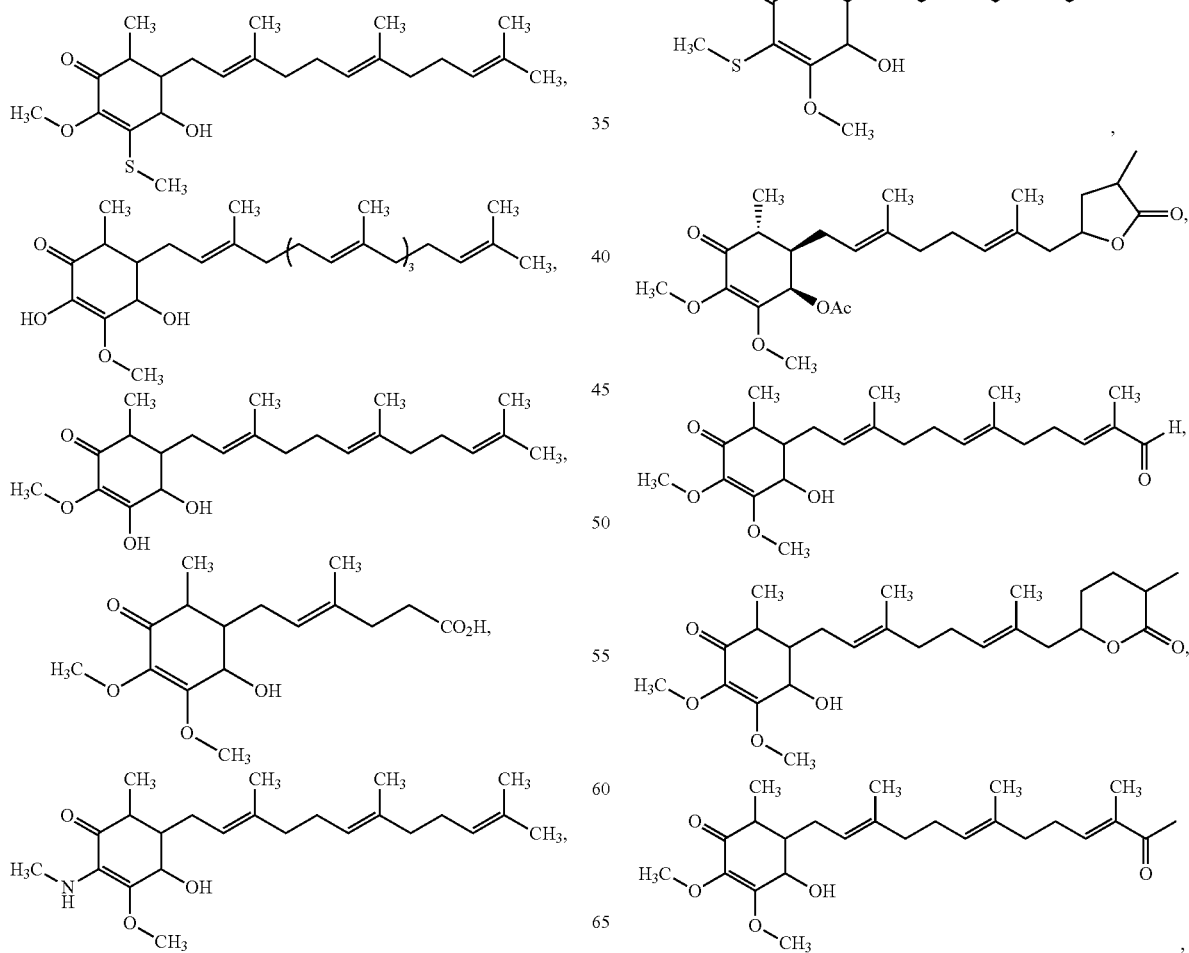
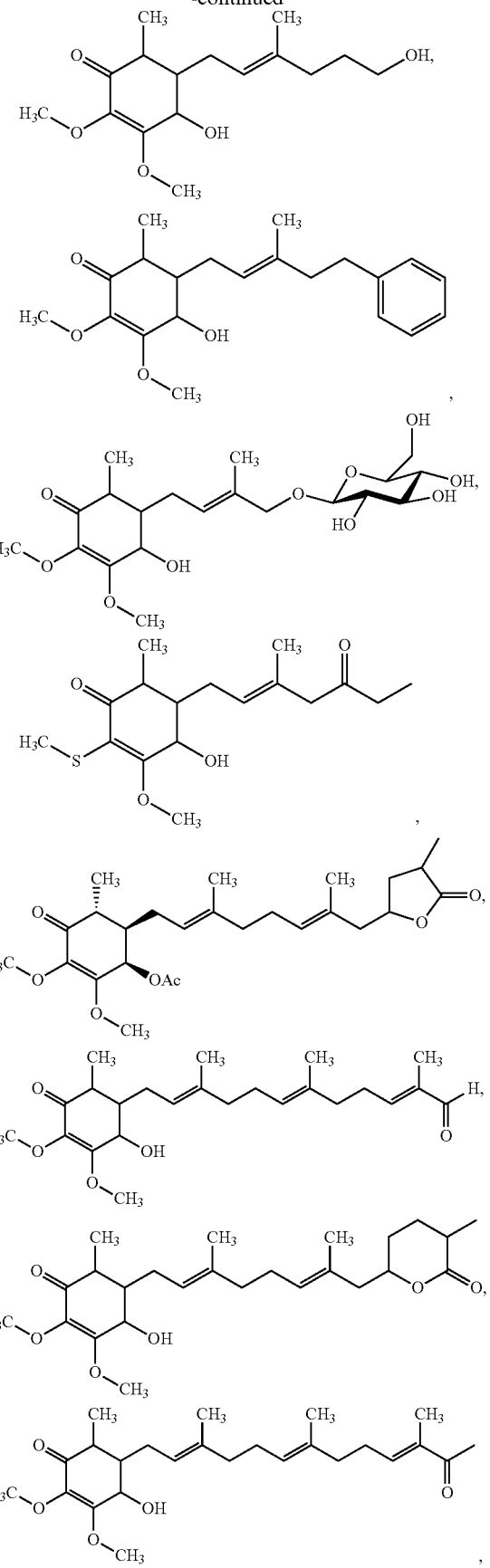

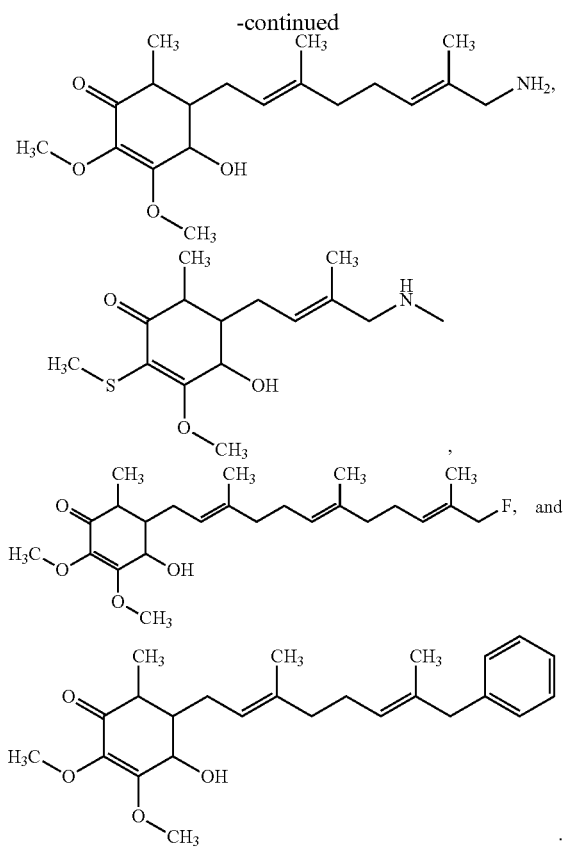

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed based on the mode of action described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein. Combinations of compounds (i.e., the cyclohexenone compound described herein) with other leukemia therapeutic agents are intended to be covered. In some embodiments, examples of leukemia therapeutic agents to bring about bone marrow remission include, but are not limited to, the following: prednisone, L-asparaginase, and vincristine, and the like. In some embodiments, examples of consolidation therapy or intensification leukemia therapeutic agents to eliminate any remaining leukemia cells include, but are not limited to, the following: methotrexate, 6-mercaptopurine (6-MP), and the like.

The combinations of the cyclohexenone compounds and other leukemia therapeutic agents described herein encompass additional therapies and treatment regimens with other agents in some embodiments. Such additional therapies and treatment regimens can include another leukemia therapy in some embodiments. Alternatively, in other embodiments, additional therapies and treatment regimens include other agents used to treat adjunct conditions associated with leukemia or a side effect from such agent in the combination therapy. In further embodiments, adjuvants or enhancers are administered with a combination therapy described herein.

In some embodiments provide compositions for treating or reducing the risk of leukemia comprising a therapeutically effective amount of a cyclohexenone compound having the structure:

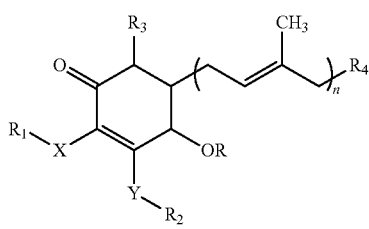

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, optionally substituted methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and n=1-12; or a pharmaceutically acceptable salt, metabolite, solvate or prodrug thereof; and one or more leukemia therapeutic agents.

EXAMPLES

Example 1

Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR ($CDC_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR ($CDC_3$) δ (ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

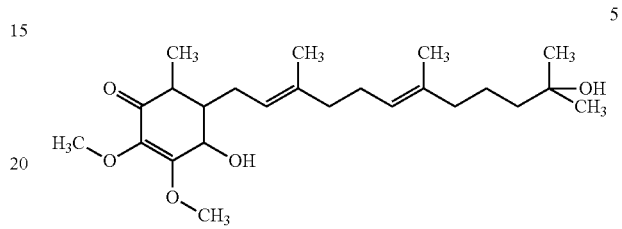

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 ($C_{25}H_{42}O_5$). $^1$H-NMR ($CDC_3$) δ (ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR ($CDC_3$) δ (ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

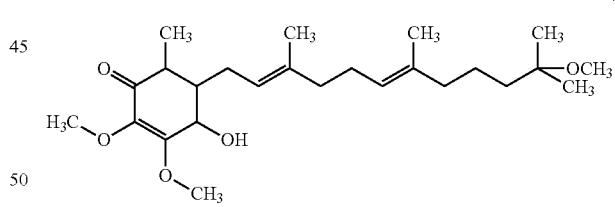

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR ($CDC_3$) δ (ppm)=1.51, 1.67, 1.71, 1.75, 1.94, 2.03, 2.07, 2.22, 2.25, 3.68, 4.05, 5.07, and 5.14; $^{13}$C-NMR ($CDC_3$) δ (ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

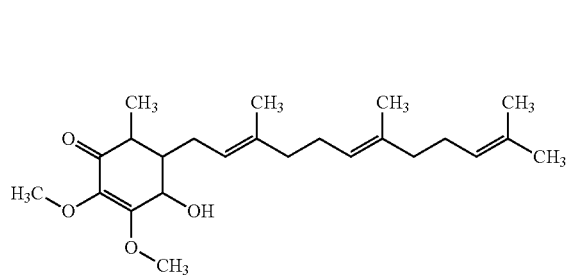

Compound 1: 4-hydroxy-2,3-dimethoxy-6-methyl-5-(3,7,11-trimethyldodeca-2,6,10-trienyl)cyclohex-2-enone Compound 27, a metabolite of compound 1, was obtained from urine samples of rats fed with Compound 1 in the animal study. Compound 27 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 25 which was determined as 2,3-dimethoxy-5-methyl-6-((2E,6E)-3,7,11-trimethyldodeca-2,6,10-trienyl)cyclohexa-2,5-diene-1,4-dione (molecular weight of 386.52, $C_{24}H_{34}O_4$), was obtained from the purification process.

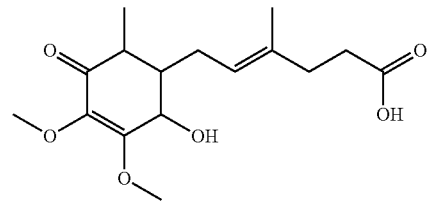

Compound 26, 4-hydroxy-2-methoxy-6-methyl-5-((2E,6E)-3,7,11-trimethyldodeca-2,6,10-trienyl)cyclohex-2-enone, was also prepared by purification process with molecular weight of 350.53 ($C_{23}H_{36}O_3$). Compound 28 was also prepared.

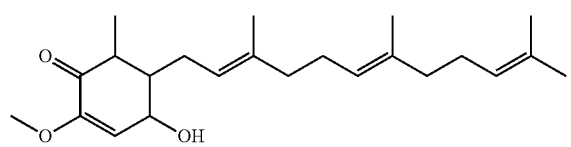

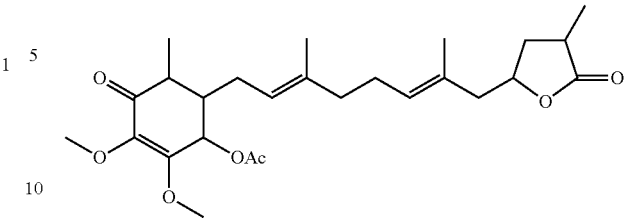

Alternatively, the exemplary compounds may be prepared from 4-hydroxy-2,3-dimethoxy-6-methylcyclohexa-2,5-dienone, or the like. Similarly, other cyclohexenone compounds having the structure

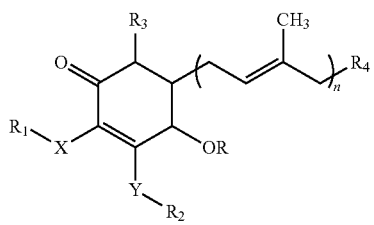

are isolated from *Antrodia camphorate* or prepared synthetically or semi-synthetically from the suitable starting materials. An ordinary skilled in the art would readily utilize appropriate conditions for such synthesis.

Example 2

Cell Lines and Cell Culture Preparation

Human hepatoma (HepG2, Hep3B), human lung adenocarcinoma (A549, H838), and human myelogenous leukemia (K562) cell lines were obtained from American Type Culture Collection (Rockville, Md., USA). Human prostate cancer cell lines (LNCaP and DU145), human breast carcinoma (MCF-7), human bladder carcinoma (TSGH 8301) and human pancreas adenocarcinoma (BxPC-3) were obtained from BCRC (Bioresource Collection and Research Center, Hsinchu, Taiwan). HepG2, DU145 and MCF-7 cell lines were cultured in Minimum Essential Medium Alpha (Invitrogen/Gibco BRL, Grand Island, N.Y., USA). A549 cells were cultured in Dulbecco's modified Eagle's medium (Invitrogen/Gibco BRL). H838, TSGH 8301, BxPC-3 LNCaP and K562 cell lines were cultured in RPMI-1640 medium (Invitrogen/Gibco BRL). All cells were cultured at 37° C. in 5% $CO_2$ in culture media supplemented with 10% fetal bovine serum (FBS) (Invitrogen/Gibco BRL) and 100 U/ml streptomycin and penicillin (Invitrogen/Gibco BRL). For treatment, cells were seeded in six-well plates at $6.25 \times 10^5$ cells/well. On the following day, the media was changed to serum-free media, and cells were serum-starved for 24 h. Compound 1 was dissolved in DMSO and diluted to the required concentration in serum-free medium. Cultures were then treated with diluted Compound 1 as indicated. After treatment, cells were washed with cold phosphate-buffered saline (PBS) and lysed using RIPA buffer containing phosphatase and protease inhibitors.

Example 3

Immunoblot Analysis

Sixty micrograms of total protein lysates measured using a Bradford assay (Sigma-Aldrich, St. Louis, Mo., USA) were resolved on 12.5% SDS-polyacrylamide gels. Electrophoresis was performed at a constant voltage of 180 V for 50 minutes (min). Gels were transferred onto PVDF membranes at a constant current of 280 mA for 90 min. Blots were blocked with 3% bovine serum albumin (BSA) and probed with a 1:1,000 dilution of antibodies against phospho-p44/42 (ERK1/2) (Thr202/Tyr204) (Cell Signaling Technology, Danvers, Mass., USA), p44/42MAPK (ERK1/2), Beclin-1 (Cell Signaling Technology), LC3B (Novus Biologicals, Cambridge, UK), EGFR (Epitomics Inc, Santa Clara, Calif.), Ras, GAPDH, or β-actin (Sigma-Aldrich). Secondary antibodies were conjugated to horseradish peroxidase, which was detected using a 3,3'-diaminobenzidine substrate kit (Vector Laboratories, Burlingame, Calif.). The immunoreactive bands were quantified by densitometry using Image-Pro Plus software (Media Cybernetics, Silver Spring, Md.).

Example 4

CCK-8 Cell Viability Assay

Cell Counting Kit-8 (CCK-8) allows sensitive colorimetric assays for the determination of cell viability in cell proliferation and cytotoxicity assays. The detection sensitivity of CCK-8 is higher than the other tetrazolium salts such as MTT, XTT, MTS or WST-1.

Cell viability was measured using Cell Counting Kit-8 (CCK-8, Enzo Life Sciences, Farmingdale, N.Y.). In this assay, WST-8 is reduced by dehydrogenases in cells to produce a yellow-colored product (formazan), which is soluble in culture medium. The amount of formazan generated is directly proportional to the number of living cells. After treatment, CCK-8 solution was added to each well and incubated for 4 h. The concentration of formazan was measured with a spectrophotometer at an absorbance wavelength of 450 nm. Cell viability was expressed as a percentage of the corresponding control.

Example 5

SDS-PAGE-Based Prenyltransferase Assay

In vitro prenylation reactions were performed in 20 µl reaction buffer (50 mM HEPES, pH 7.2, 50 mM NaCl, 5 mM MgCl$_2$, 5 mM DTT, and 20 µM GDP) mixed with 3 µg FTase (Jena, Germany), 25 µM NBD-FPP, and 2 µg H-Ras$^{GST}$ in the presence or absence of various concentrations of Antroquinonol. Reactions were incubated for 3 h at 37° C. and quenched by adding 20 µl 2×SDS-PAGE sample buffer and boiling at 95° C. for 3 min. Finally, the mixtures were resolved by 15% SDS-PAGE. The gel was scanned using a Typhoon 9400 scanner (GE Healthcare, UK) (excitation laser, 473 nm; emission cutoff filter, 510 nm) followed by staining with Coomassie blue. The fluorescent bands were quantified using Image-Pro Plus software (Media Cybernetics, Silver Spring, Md., USA).

Example 6

Immunofluorescent and DAPI Staining

Cells were seeded onto glass coverslips in six-well plates. After an overnight incubation, cells were treated with the indicated concentrations of Compound 1 for 24 h. After treatment, cells were fixed with 4% paraformaldehyde in PBS for 5 min and permeabilized with 0.1% Triton X-100 in PBS for 5 min. Cells were incubated in 3% BSA as a blocking agent for 30 min. Cells were then incubated with a rabbit polyclonal antibody against LC3B (Sigma-Aldrich) at room temperature for 90 min. After washing three times consecutively with 0.1% Triton X-100 in PBS, cells were incubated with a fluorescein isothiocyanate-conjugated secondary antibody (Invitrogen Life Technologies, Paisley, Scotland, UK) at room temperature for 60 min. Cells were mounted with Dapi-Fluoromount-G™ (SouthernBiotech, Birmingham, Ala., USA) and visualized by confocal fluorescence microscopy using a Zeiss LSM 780 plus ELYRA S.1.

Example 7

Determination of the Cytotoxic Effects of Compound 1 and its Derivatives, Analogues, and a Metabolite To determine whether the cytotoxic effects of Compound 1 correlate with the presence of Ras mutations, cell lines derived from human lung cancer (A549 and H838), liver cancer (HepG2 and Hep3B), and leukemia (K562 and THP-1) with wild-type Ras (H838, Hep3B, and K562) or mutant Ras (A549, HepG2, and THP-1) were used. Cell viability was measured after 48 h of Compound 1 treatment. The cell lines and their IC$_{50}$s in increasing order were THP-1 (2.22 µM)<A549 (3.24 µM)<H838 (3.32 µM)<Hep3B (3.74 µM)<K562 (5.12 µM)<HepG2 (6.42 µM) (Table 1). Thus, sensitivity to Compound 1 did not correlate with Ras gene status, as Compound 1 exhibited excellent cytotoxic activity in all cell lines described herein.

TABLE 1

IC$_{50}$ values of exemplary compounds of formula X determined by CCK-8 cell viability assay.

| Compound | A549 | H838 | Hep3B | HepG2 | K562 | THP-1 |
| --- | --- | --- | --- | --- | --- | --- |
| 1 | 3.24 ± 0.35 | 2.96 ± 0.05 | 3.74 ± 0.35 | 6.42 ± 0.08 | 5.12 ± 0.83 | 2.22 ± 0.03 |
| 25 | — | 22.56 ± 6.45 | — | — | — | — |
| 26 | — | 11.34 ± 4.17 | — | — | — | — |
| 27 | — | >100 | — | — | — | — |
| 28 | — | >100 | — | — | — | — |
| 29 | — | >100 | — | — | — | — |
| 30 | 22.61 ± 2.24 | 25.56 ± 6.54 | 9.06 ± 3.03 | 27.03 ± 6.06 | — | — |
| 31 | 6.68 ± 0.75 | 3.41 ± 1.43 | 7.46 ± 7.06 | 8.98 ± 0.97 | — | — |

Values were presented as means ± S.E.M.

The results indicate that sensitivity to exemplary Compound 1 did not correlate with Ras gene status, as Compound 1 exhibited excellent cytotoxic activity in all cell lines. Furthermore, based on the $IC_{50}$ values for Compound 1 analogs (Compounds 25 to 31) in H838 cells indicated that the 2'-hydroxy group and the farnesyl group of Compound 1 were important for its cytotoxic effects.

Example 8

Evaluation of the Impact of Compound 1 on Level of Phosphorylated ERK1/2

Figure 1:
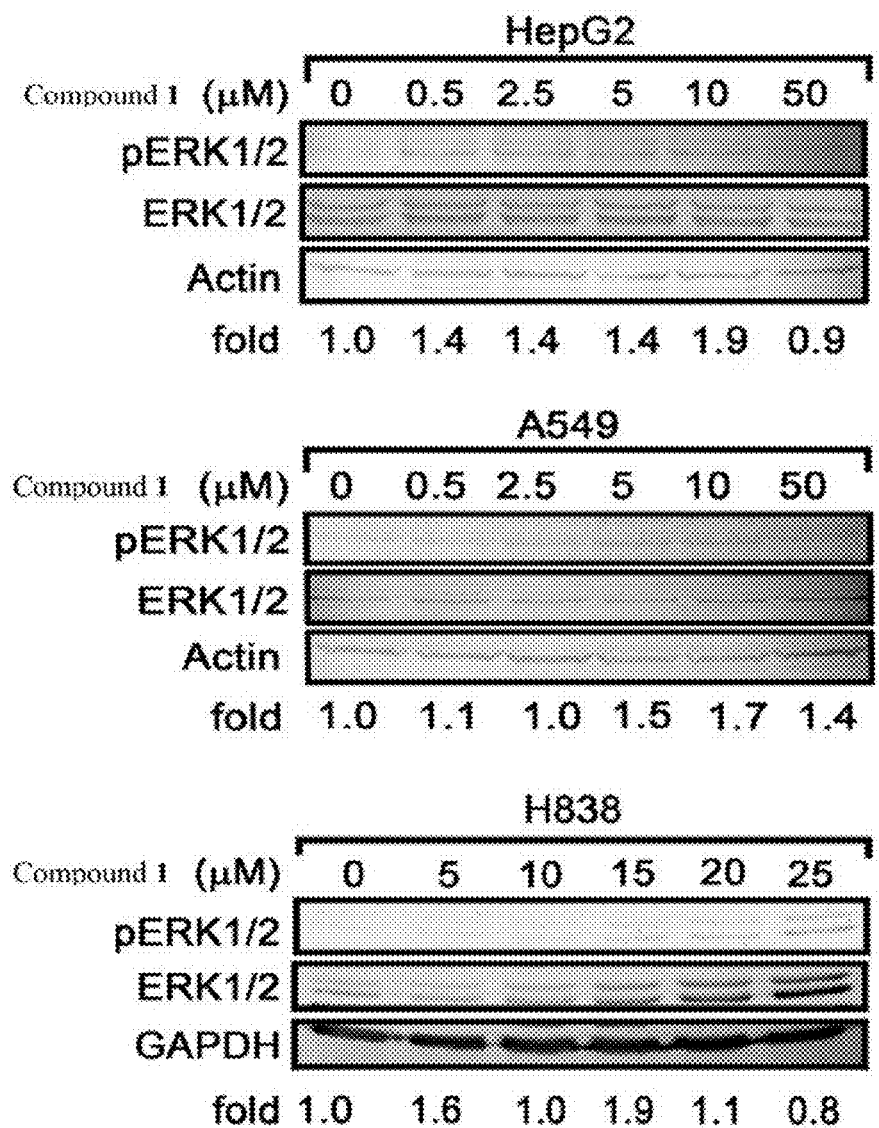
FIG. 1 shows exemplary results of Compound 1 stimulates ERK phosphorylation in HepG2, A549, and H838 cell lines. HepG2, A549, and H838 cell lines were serum-starved overnight and challenged with the indicated concentrations of Compound 1 for 1 h. Whole cell lysates were then immunoblotted with a phospho-ERK1/2 antibody and re-probed with an antibody against β-actin. A duplicate membrane was probed with a total ERK1/2 antibody. The relative expression level of p-ERK1/2 to β-actin was quantified by densitometry. Experiments were conducted in triplicate.

To evaluate the impact of Compound 1 on MAP kinase signaling, HepG2, A549, and H838 cells were treated with a wide range of Compound 1 concentrations, and immunoblots for phosphorylated and total ERK1/2 were performed. Compound 1 induced phosphorylation of ERK1/2 in HepG2 and A549 cells, whereas the total ERK1/2 expression level was unaffected (FIG. 1). However, in H838 cells, the increase in ERK1/2 phosphorylation after Compound 1 treatment was coincident with increased expression of total ERK1/2. Thus, in general, Compound 1 induced an increase in ERK1/2 phosphorylation in cancer cell lines.

Example 9

Study of ERK1/2 Phosphorylation in A549 Cells by Compound 1

In a previous report, Compound 1 was shown to inhibit PI3K signaling in A549 cells (Kumar V B, et al., Mutat Res 2011 Feb. 10; 707(1-2):42-52). Here, it was shown that exemplary Compound 1 upregulates ERK1/2 phosphorylation in A549 cells. Ras is an upstream regulator of PI3K and ERK1/2. To better understand the cellular signaling pathways that lead to Compound 1-mediated cancer cell death and to more precisely identify the cytosolic target of Compound 1, the contribution of Ras was investigated. Experiments were conducted in serum and serum-free conditions using A549 and H838 cells, which were treated with different concentrations of Compound 1 for 24 h. Two distinct bands were detected on immunoblots probed for Ras. The slower migrating band corresponded to unprocessed Ras, whereas the faster migrating band represented fully processed Ras. Compound 1 caused an accumulation of unprocessed Ras in both cell lines in serum and serum-free conditions (FIG. 2A). Furthermore, Compound 1 caused a dose-dependent accumulation of unprocessed Ras in H838, HepG2 and K562 cells (FIGS. 2B and 2C). The results show that Compound 1 inhibits Ras processing in cancer cells.

Example 10

Figure 3:
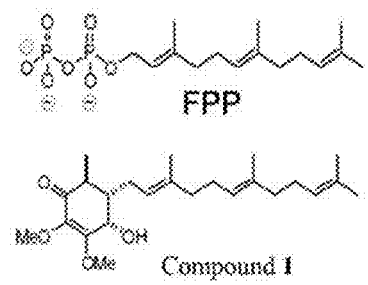
FIG. 3A-C show illustrative effective results of Compound 1 inhibiting the prenylation activity of farnesyltransferase in vitro and competes with FPP within cells. (3A) Chemical structure of Compound 1 and FPP. (3B) H838 cells stimulated with either Compound 1 or FPP as indicated for 24 h. Whole cell lysates were then immunoblotted with a Ras antibody. A duplicate membrane was probed with a GAPDH antibody. The relative expression level of unprocessed to processed Ras was quantified by densitometry. The experiments were conducted three times. (3C) SDS-PAGE of fluorescently labeled H-Ras-GST after prenylation with NBD-FPP mediated by FTase. The lower panel shows the same gel stained with Coomassie blue.
Figure 3:
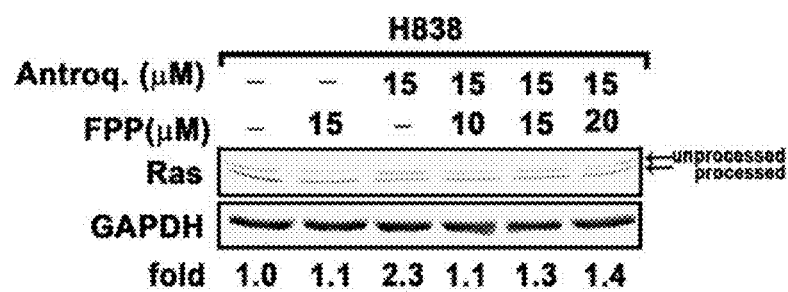
Figure 3:
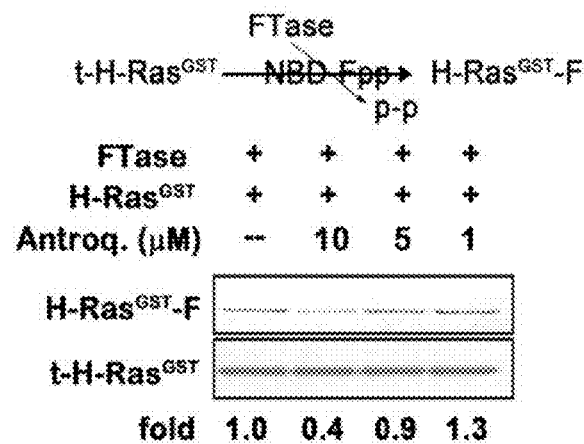

Evaluating the Effects of Compound 1 on Protein FTase Activity and FPP-Dependent Ras Prenylation in Cell Culture Posttranslational modification of Ras is essential for its activation. The first step committing Ras to become active is prenylation by the enzyme FTase. Comparison of the chemical structures of Compound 1 and FPP, which is a prenyl group donor for Ras, showed that both compounds have the same C15 lipid chain (FIG. 3A). Thus, the effects of Compound 1 on protein FTase activity and FPP-dependent Ras prenylation in cell culture were evaluated. The results indicated that Compound 1 alone significantly enhanced accumulation of unprocessed Ras. Further, FPP alone potentiated Ras processing in H838 cells. Competition assays showed that FPP neutralized the effect of Compound 1 on Ras processing at concentrations as low as 10 μM (FIG. 3B). In addition, an in vitro enzymatic activity assay demonstrated that Compound 1 achieved dose-dependent inhibition of FTase activity (FIG. 3C). The results show that Compound 1 inhibits protein FTase activity and is competitive with FPP in cell culture.

Example 11

Molecular Docking of Compound 1 on Protein FTase

The amino acid sequence for FTase (Accession no.: 1JCQ_A) was downloaded from the National Center for Biotechnology Information protein database. A CDOCKER-A CHARMm-based molecular docking algorithm was applied to predict and assess the interaction between Compound 1 and the FTase CAAX box (see e.g. Wu G, et al., Vieth M (2003) Detailed analysis of grid-based molecular docking: A case study of CDOCKER-A CHARMm-based MD docking algorithm. Journal of Computational Chemistry 24 (13): 1549-1562). In order to limit bias, all user-adjustable parameters were kept at their default settings.

Figure 4A:
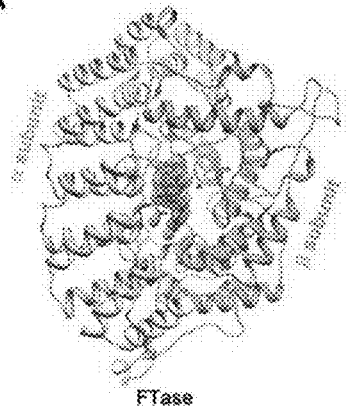
FIG. 4A-D show the model structure of human FTase in complex with Compound 1, CIFM-derived L739, 750 peptidomimetic, and FPP substrate. (4A) Ribbon cartoons of FTase complexed with Compound 1. (4B) Simultaneous binding of Compound 1 (green) and FPP (purple) to FTase. (4C) Ribbon cartoons of FTase complexed with Antroquinonol. Putative hydrogen bonds are represented by dashed lines. (4D) Ribbon cartoons of FTase complexed with Compound 1 and CIFM-derived L739,750.
Figure 4B:
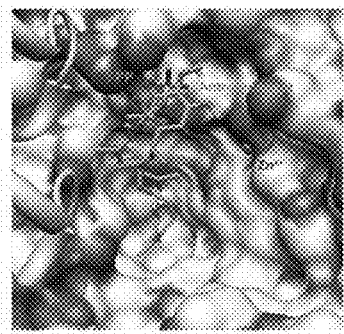

To predict the putative interactions between FTase and exemplary cyclohexenone compounds described herein (e.g., Compound 1), a molecular docking approach was conducted using the Dock Ligands (CDOCKER) program. Using the crystal structure of FTase (PDB ID 1JCQ) as a template, we built a docking model to characterize the interaction between Compound 1 and the CAAX motif in FTase. Docking studies showed that Compound 1 and FPP bind in a similar orientation to the FTase active site (FIG. 4A-B). The farnesyl group of Compound 1 lies in the hydrophobic cavity and interacts with a number of conserved aromatic residues. The ring structure with the functional groups of Compound 1 and the diphosphate moiety of FPP are located near the α/β-subunit interface. The cytotoxic effects of the Compound 1 analogues indicate that the length of the isoprene unit and the 2'-hydroxy group play vital roles in mediating cytotoxic activity.

Figure 4C:
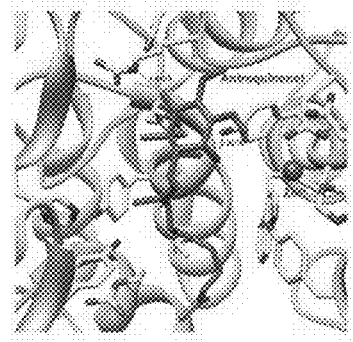
Figure 4D:
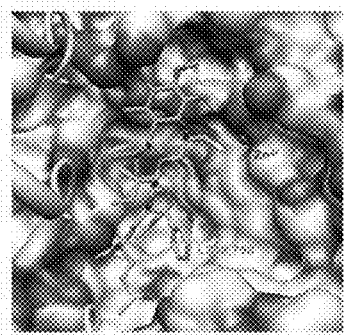

The docking model can also be used to explain differences in the cytotoxic profiles of Compound 1 analogues. It has been shown that the number of isoprene units influences the binding affinity of isoprenoids for FTase. The 2'-hydroxy group of Compound 1 may form intermolecular hydrogen bonds with the tyrosine residue, Y300b (FIG. 4C). In addition, the spatial arrangement of the ring structure of Compound 1 indicated that the 3-methoxy group is located in an unoccupied space near the interface of the FTase subunits. Thus, it is likely that demethoxy-Compound 1 would show an $IC_{50}$ only slightly less than the prototype, Compound 1. These results provide important structural insights into the specific architecture of Compound 1 and the CAAX motif in FTase (FIG. 4D), which will help with the rational design of active cyclohexenone compounds described herein (e.g., Compound 1 analogues).

Example 12

Compound 1 Enhanced Autophagic Activity in Cancer Cells

Figure 5A:
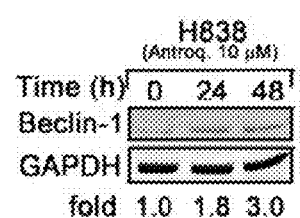
FIG. 5A-C show illustrative effective results of Compound 1 inducing autophagic activity in H838 cells. H838 cells were treated with different concentrations of Compound 1 and grown under serum-free conditions. (5A) Cells were harvested at 0, 24 and 48 h following treatments and subjected to immunoblotted with Beclin-1 antibody. (5B) Whole cell lysates were prepared at 24 h following treatments and subjected to immunoblotted with an LC3B antibody. A duplicate membrane was probed with a GAPDH antibody. The relative expression level of LC3B-I to LC3B-II was quantified by densitometry. (5C) The distribution of endogenous LC3B in autophagosomes was detected by confocal microscopy. The experiments were conducted three times. Bars represent the mean±SEM. *P<0.05, ** P<0.01
Figure 5B:
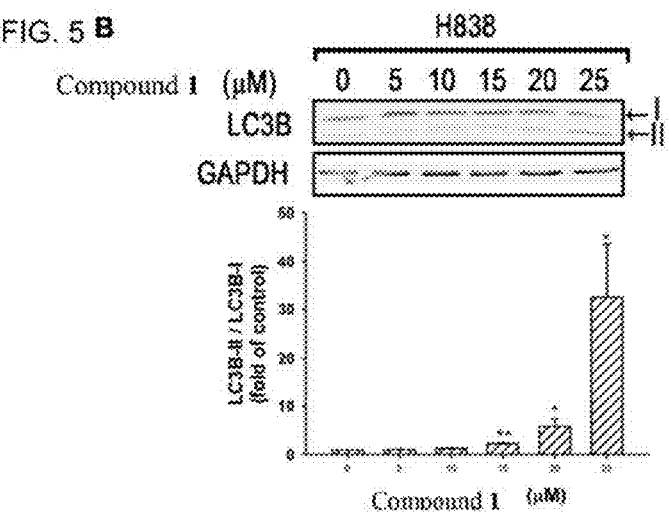
Figure 5C:
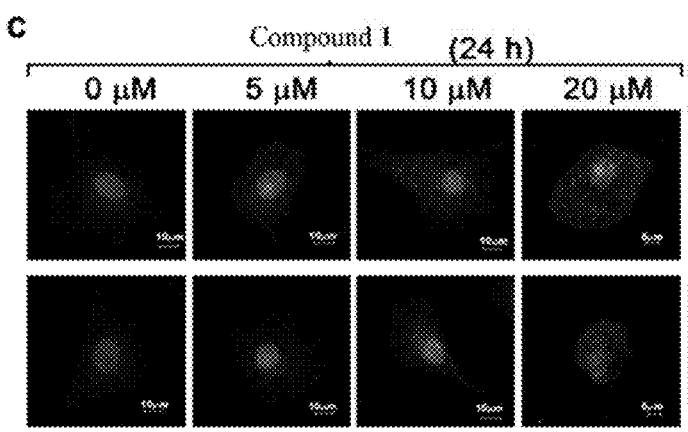
Figure 6:
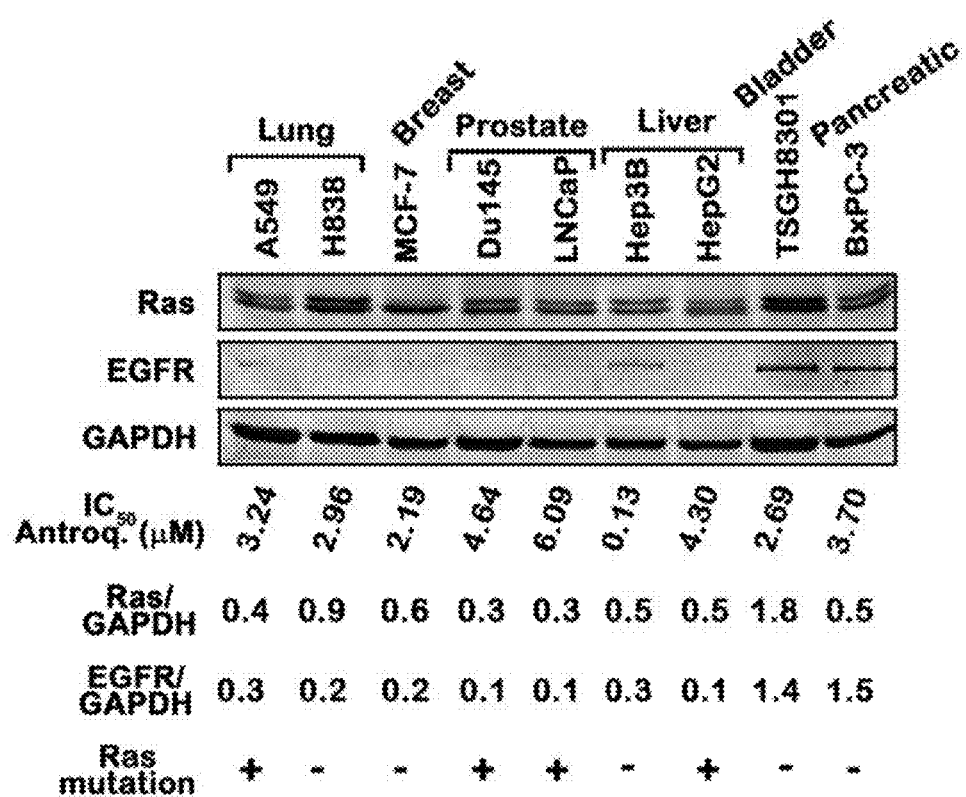
FIG. 6 shows illustrative correlation between the cytotoxic activity of Compound 1 with protein levels of Ras and EGFR in cancer cell lines. Whole cell lysates were resolved by SDS-PAGE and immunoblotted with a Ras antibody. Duplicate membranes were probed with an antibody against EGFR or GAPDH. The experiments were conducted three times.

Our previous investigations indicated that Compound 1 induces apoptosis and/or autophagic cell death in human cancer cell lines via the PI3K/mTOR pathway. Ras lies upstream of PI3K and has been demonstrated to negatively regulate autophagic activity in RasVal12-transformed NIH3T3 cells. Here, the level of Compound 1-induced autophagy in a lung cancer cell line was measured by immunoblot analysis of Beclin-1 and LC3B. LC3B-containing autophagosomes were visualized by confocal microscopy. The results indicated that Beclin-1 expression increased at 24 h and 48 h after Compound 1 treatment (FIG. 5A-B). Compound 1 also induced autophagic conversion of LC3B-1 to LC3B-II. Further, LC3B-II-associated autophagosomes (green fluorescent spots) were observed by confocal microscopy (FIG. 5C).

Statistical Analysis

Results of the Examples were expressed as the mean±standard error of the mean (SEM) of three independent experiments. A single factor pair-wise ANOVA statistical analysis was conducted to determine the significance in differences. A two-tailed P-value of less than 0.05 was considered significant.

Example 13

Efficacy Test of Compound 1 on Leukemia Cancer Xenograft Model

Six to seven weeks old male CB.17 SCID mice were purchased from BioLasco Taiwan Co., LTD. and quarantined for one week. During experiment period, 5 mice will be housed in one cage. All animals will be hosted in the Da-Hu animal facility in a 12-h light/12-h dark cycle at 19-25° C. Animals have free access to rodent pellet food and water ad libitum. The experimental protocol of animal study was reviewed and approved by the Institutional Animal Care and Use Committee, DCB. Compound 1 was diluted in olive oil to final concentrations of 12 mg/mL.

Tumor cell line: THP-1 cells (leukemia) were cultured in RPMI-1640 medium or DMEM medium which supplemented with 10% heat inactivated fetal bovine serum. The cells were cultured in tissue culture flasks in a humidified incubator at 37° C., in an atmosphere of 5% $CO_2$ and 95% air.

In Vivo Implantation

The human cancer cells used for implantation were harvested during log phase growth and resuspended in phosphate buffered saline to a concentration containing $2 \times 10^7$ cells/mL of THP-1, in 0.1 mL of a 50% Matrigel solution (BD Biosciences, MA, USA). When the average tumor volume had reached 150 mm$^3$, the mice were randomly divided into 2 groups and were administrated with test articles. Volume was calculated using the formula:

Tumor Volume=$(w^2 \times l)/2$ where w=width and l=length in diameter (mm) of the tumor.

Treatment

The following table presents a summary of the treatment plan. All treatments of Compound 1 were administered by oral gavage (PO) twice/day (bID) and 5 days/week for 4 weeks. All doses were administered in a volume of 10 mL/kg body weight. Vehicle group received the same volume of olive oil served as control group for calculation of tumor growth inhibition rate.

| Treatment Regimen | | | | | |
|---|---|---|---|---|---|
| Group | N | Agent | Dose | Route | Schedule |
| 1 | 5 | Vehicle (olive oil) | — | PO | bID × 5 days/wk × 4 wk |
| 2 | 5 | Compound 1 | 120 mg/kg | PO | bID × 5 days/wk × 4 wk |

Assessments of Tumor Volume and Body Weight

Tumors were measured twice per week using calipers. The percentage of tumor growth inhibition (TGI) was calculated using the following formula:

% TGI=[1−(T/C)]×100% where T and C represent the mean tumor volumes of the treatment group and the control group, respectively. Animals were weighed twice weekly until the completion of the study. The body weight change was calculated as the percentage increase in body weight compared to the initial body weight.

Data Analysis

Data was expressed as mean±SEM. Comparisons between two groups were performed using Student's t test. A p value <0.05 was considered statistically significant difference.

Results

Figure 8:
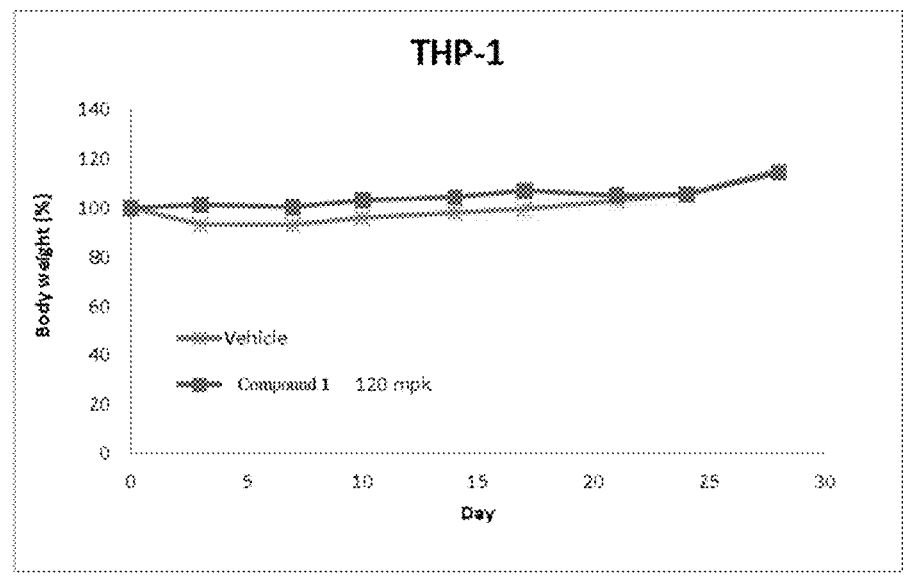
FIG. 8 shows illustrative results by body weight of THP-1 xenograft mice treated with Compound 1. The tumor-bearing THP-1 xenograft mice were treated with vehicle (olive oil) or Compound 1 at 120 mg/kg by oral gavage twice per day and 5 days per week for 4 weeks. The body weight was measured twice weekly.

FIG. 8 shows almost no body weight changes of THP-1 xenograft mice treated with test compound. The tumor-bearing mice were treated with vehicle (olive oil) or Compound 1 at 120 mg/kg by oral gavage twice per day and 5 days per week for 4 weeks. The body weight was measured twice weekly.

Figure 9:
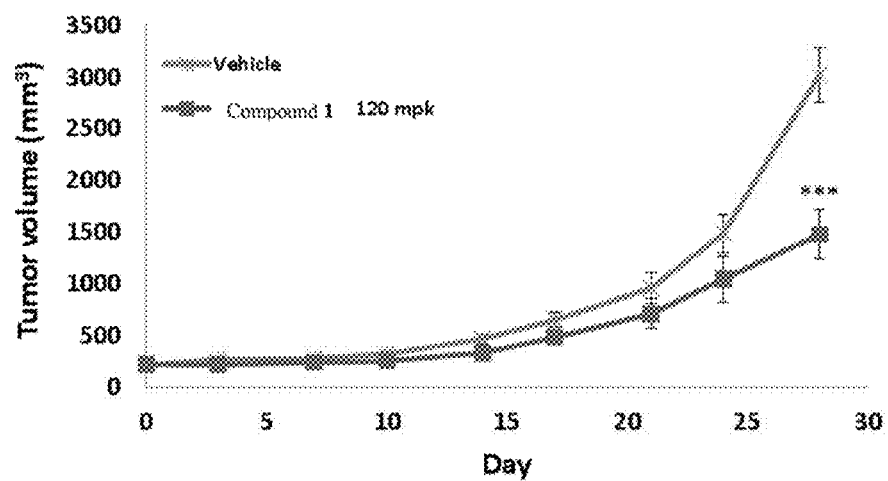
FIG. 9 shows illustrative results by tumor volume of THP-1 xenograft mice treated with Compound 1. The tumor-bearing mice were treated with vehicle (olive oil) or Antroquinonol at 120 mg/kg by oral gavage twice per day and 5 days per week for 4 weeks. The tumor volume was measured twice weekly. ***P<0.005 compared to vehicle control.

FIG. 9 shows decrease of the tumor volume of THP-1 xenograft mice treated with test compound. The tumor-bearing mice were treated with vehicle (olive oil) or Antroquinonol at 120 mg/kg by oral gavage twice per day and 5 days per week for 4 weeks. The tumor volume was measured twice weekly. ***P<0.005 compared to vehicle control.

Figure 10:
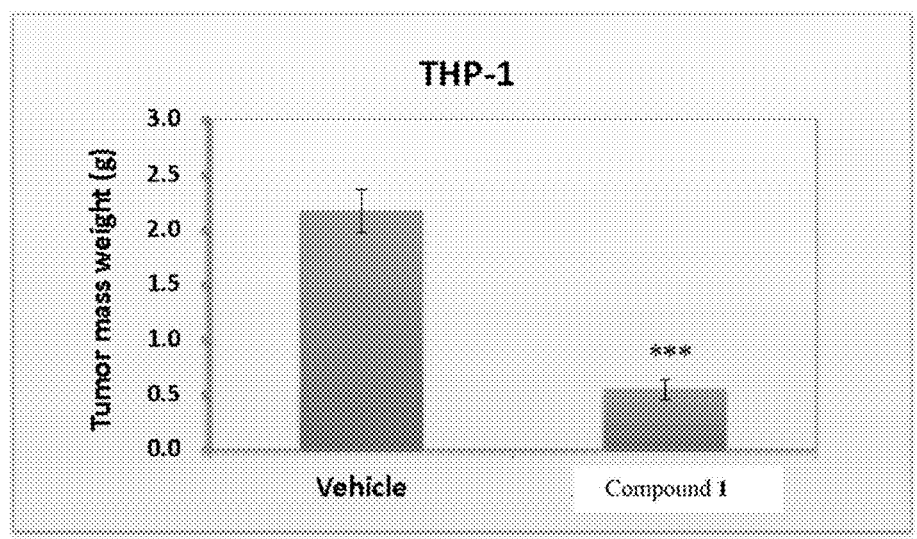
FIG. 10 shows illustrative results by tumor mass weight of THP-1 xenograft mice treated with Compound 1. The tumor-bearing mice were treated with vehicle (olive oil) or Antroquinonol at 120 mg/kg by oral gavage twice per day and 5 days per week for 4 weeks. The tumor mass weight was measured after treatment.

FIG. 10 shows the decrease tumor mass weight at the end point of THP-1 xenograft mice treated with test compound.

These results clearly demonstrate the effectiveness and efficacy exemplary invention Compound 1 on leukemia cancer treatment based on xenograft model.

Example 14

Use of Compound 1 for Treating Patients with Acute Myeloid Leukemia, Myelodysplasia, Non-Hodgkin's Lymphoma, or Multiple Myeloma Clinical trial to study the effectiveness of the cyclohexenone compounds described herein such as Compound 1 in treating patients who have acute myeloid leukemia, myelodysplasia, non-Hodgkin's lymphoma or multiple myeloma.

Study Type: Interventional
Study Design: Masking: Open Label
Primary Purpose: Treatment
Objectives:
Determine the ability of Compound 1 in treating patients who have acute myeloid leukemia, myelodysplasia, non-Hodgkin's lymphoma or multiple myeloma.

Determine the effect of this treatment regimen in these patients.

Determine the safety and potential antitumor efficacy of this treatment regimen in these patients.

OUTLINE: Patients receive Compound 1 orally on days 1-12. Patients with acute myeloid leukemia who respond to therapy may receive a second course approximately 10 days after the end of the first. Subsequent courses in these patients, and all additional courses in all other patients, are repeated every 21 to 28 days in the absence of disease progression or unacceptable toxicity.

Eligibility
Ages Eligible for Study: 18 Years and older
Genders Eligible for Study: Both
PROJECTED ACCRUAL: A total of 20 patients will be accrued for this study.

Criteria
  Disease Characteristics:
    Diagnosis of one of the following neoplastic diseases:
    Acute myeloid leukemia
    Myelodysplasia
    Low or intermediate grade non-Hodgkin's lymphoma
    Multiple myeloma
    Failed prior conventional therapy and no other known curative therapy exists
    Patients with non-Hodgkin's lymphoma must have tumor cells in bone marrow or malignant effusions that are accessible for bone marrow aspiration or paracentesis/thoracentesis NOTE: A new classification scheme for adult non-Hodgkin's lymphoma has been adopted by PDQ. The terminology of "indolent" or "aggressive" lymphoma will replace the former terminology of "low", "intermediate", or "high" grade lymphoma. However, this protocol uses the former terminology.
Patient Characteristics:
  Age: 18 and over
  Performance status: Karnofsky 60-100%
  Life expectancy: Not specified
  Hematopoietic: Patients without leukemia or myeloma: WBC at least 2,500/mm$^3$; Platelet count at least 75,000/mm$^3$
  Hepatic: Bilirubin no greater than 2.5 mg/dL
  Renal: Creatinine no greater than 2.5 mg/dL
  Other: Not pregnant or nursing; Negative pregnancy test; Fertile patients must use effective contraception during and for 4 weeks after study
  Prior Concurrent Therapy:
  Biologic therapy: Not specified
  Chemotherapy: Patients without leukemia: At least 3 weeks since prior cytotoxic chemotherapy
  Endocrine therapy: Not specified
  Radiotherapy: Patients without leukemia: At least 3 weeks since prior radiotherapy
  Surgery: Not specified Example 15

Oral Formulation

To prepare a pharmaceutical composition for oral delivery, 100 mg of an exemplary Compound 1 was mixed with 100 mg of corn oil. The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 16

Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 17

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating or reducing the risk of leukemia in a subject comprising administering to said subject a therapeutically effective amount of a cyclohexenone compound having the structure:

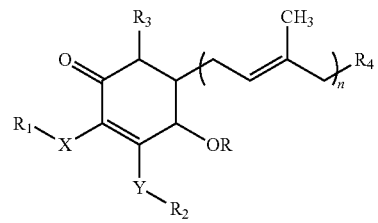

wherein each of X and Y independently is oxygen, NR$_5$ or sulfur;
R is a hydrogen or C(=O)C$_1$-C$_8$alkyl;
each of R$_1$, R$_2$ and R$_3$ independently is a hydrogen, optionally substituted methyl or (CH$_2$)$_m$—CH$_3$;
R$_4$ is NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl,
wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;
each of R$_5$ and R$_6$ is independently a hydrogen or C$_1$-C$_8$alkyl;
R$_7$ is a C$_1$-C$_8$alkyl, OR$_5$ or NR$_5$R$_6$;
m=1-12; and
n=1-12; or a pharmaceutically acceptable salt, metabolite, solvate or prodrug thereof.

2. The method of claim 1, wherein the leukemia is an acute leukemia.

3. The method of claim 1, wherein the leukemia is chronic leukemia.

4. The method of claim 2, wherein the acute leukemia is an acute myeloid leukemia, acute erythroid leukemia, acute lymphoblastic leukemia, T-cell acute lymphoblastic leukemia, adult T-cell leukemia/lymphoma, precursor T acute lymphoblastic leukemia/lymphoma, or blast crisis of chronic myelogenous leukemia.

5. The method of claim 3, wherein the chronic leukemia is a chronic myelogenous leukemia, chronic lymphocytic leukemia, hairy cell leukemia.

6. The method of claim 5, wherein the chronic leukemia is a chronic myelogenous leukemia.

7. The method of claim 1, wherein said cyclohexenone compound, or a pharmaceutically acceptable salt, metabolite, solvate or prodrug thereof, is administered orally, parenterally or intravenously.

8. The method of claim 1, wherein said cyclohexenone compound, or a pharmaceutically acceptable salt, metabolite, solvate or prodrug thereof, is administered by injection.

9. The method of claim 1, wherein said cyclohexenone compound, or a pharmaceutically acceptable salt, metabolite, solvate or prodrug thereof, is administered orally.

10. The method of claim 1, wherein said subject is human.

11. The method of claim 1, wherein said compound is isolated from *Antrodia camphorata*.

12. The method of claim 1, wherein R is a hydrogen, $C(=O)C_3H_8$, $C(=O)C_2H_5$, or $C(=O)CH_3$.

13. The method of claim 1, wherein each of $R_1$, $R_2$ and $R_3$ independently is a hydrogen, methyl, ethyl, propyl, butyl, pentyl, hexyl, heptyl, or octyl.

14. The method of any one of claim 13, wherein $R_1$ is a hydrogen or methyl.

15. The method of any one of claim 13, wherein $R_2$ is a hydrogen or methyl.

16. The method of claim 1, wherein $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$.

17. The method of claim 1, wherein $R_4$ is $C_2H_5C(CH_3)_2OH$, $C_2H_5C(CH_3)_2OCH_3$, $C_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein the 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

18. The method of claim 1, wherein $R_4$ is $C_1$-$C_8$ alkyl optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

19. The method of claim 18, wherein $R_4$ is $CH_2CH=C(CH_3)_2$.

20. The method of claim 1, wherein said compound is

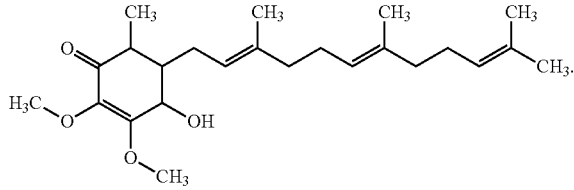 [SMILES: COC1=C(OC)C(O)C(C/C=C(\C)CC/C=C(\C)CCC=C(C)C)C(C)C1=O]

* * * * *